US010307773B2

(12) United States Patent
Colrat et al.

(10) Patent No.: US 10,307,773 B2
(45) Date of Patent: Jun. 4, 2019

(54) COATING SYSTEM WITH AN ULTRASONIC HEAD

(71) Applicant: EXEL INDUSTRIES, Epernay (FR)

(72) Inventors: Michel Colrat, Paris (FR); Rémi Pagot, Paris (FR); Robb Engle, Paris (FR)

(73) Assignee: Exel Industries, Epernay (FR)

( * ) Notice: Subject to any disclaimer, the term of this patent is extended or adjusted under 35 U.S.C. 154(b) by 0 days.

(21) Appl. No.: 15/651,836

(22) Filed: Jul. 17, 2017

(65) Prior Publication Data

US 2018/0029052 A1 Feb. 1, 2018

(30) Foreign Application Priority Data

Jul. 27, 2016 (EP) ..................... 16305971

(51) Int. Cl.
| | |
|---|---|
| *B05B 5/08* | (2006.01) |
| *B05B 5/10* | (2006.01) |
| *B05B 17/06* | (2006.01) |
| *B05B 5/025* | (2006.01) |
| *B05B 5/043* | (2006.01) |
| *B05B 5/053* | (2006.01) |
| *B05B 7/08* | (2006.01) |
| *B05D 1/04* | (2006.01) |
| *B05D 1/00* | (2006.01) |
| *H01T 19/02* | (2006.01) |

(52) U.S. Cl.
CPC ............ *B05B 5/0533* (2013.01); *B05B 5/025* (2013.01); *B05B 5/0531* (2013.01); *B05B 5/087* (2013.01); *B05B 5/10* (2013.01); *B05B 7/0815* (2013.01); *B05B 17/06* (2013.01); *A61L 2420/02* (2013.01); *B05B 5/043* (2013.01); *B05B 5/082* (2013.01); *B05D 1/005* (2013.01); *B05D 1/04* (2013.01); *H01T 19/02* (2013.01)

(58) Field of Classification Search
None
See application file for complete search history.

(56) References Cited

U.S. PATENT DOCUMENTS

| | | | |
|---|---|---|---|
| 4,377,603 A | * | 3/1983 | Itoh ......................... B05B 5/087 118/627 |
| 4,929,319 A | | 5/1990 | Dinter et al. |

(Continued)

FOREIGN PATENT DOCUMENTS

| | | |
|---|---|---|
| EP | 0253539 A2 | 1/1988 |
| EP | 1110617 A1 | 6/2001 |

(Continued)

OTHER PUBLICATIONS

European Search Report issued for European patent application No. 16305971, dated Apr. 28, 2017, 5 pages.

*Primary Examiner* — Binu Thomas
(74) *Attorney, Agent, or Firm* — Duane Morris LLP (57) ABSTRACT

This coating system (2) for coating a workpiece (W1) with a liquid coating product, includes an ultrasonic spray head (14) for generating droplets of coating products, an electrode (32A) for generating an electrostatic field (E) between the electrode and the ultrasonic spray head (14) and a high-voltage generator (52) connected to the electrode for supplying the electrode with high voltage. The shape of the electrode (32A) is advantageously configurable on the basis of the geometry of the workpiece (W1).

21 Claims, 9 Drawing Sheets

(56) References Cited

U.S. PATENT DOCUMENTS

| | | | | |
|---|---|---|---|---|
| 4,971,829 A | * | 11/1990 | Komura | B05B 5/087 |
| | | | | 427/196 |
| RE33,482 E | * | 12/1990 | Mulder | B05B 5/032 |
| | | | | 118/622 |
| 4,991,774 A | * | 2/1991 | Kelly | B05B 17/0607 |
| | | | | 239/13 |
| 5,026,463 A | * | 6/1991 | Dinter | B29C 59/12 |
| | | | | 118/620 |
| 2009/0032612 A1 | * | 2/2009 | Kunstmann | B05B 17/0607 |
| | | | | 239/102.2 |
| 2009/0181159 A1 | | 7/2009 | Pacetti | |
| 2010/0006027 A1 | * | 1/2010 | Yang | B05B 5/082 |
| | | | | 118/671 |
| 2010/0143603 A1 | * | 6/2010 | Fulkerson | B05B 5/087 |
| | | | | 118/622 |
| 2010/0297213 A1 | * | 11/2010 | Dupont | B05B 5/087 |
| | | | | 427/2.31 |
| 2013/0034723 A1 | | 2/2013 | Kalwar | |
| 2013/0284833 A1 | | 10/2013 | Fritz et al. | |

FOREIGN PATENT DOCUMENTS

| | | |
|---|---|---|
| FR | 2657794 A1 | 8/1991 |
| JP | H06-106096 A | 4/1994 |
| JP | H09-1004 A | 1/1997 |
| JP | 2004-148239 A | 5/2004 |
| WO | 2010/097539 A1 | 9/2010 |

\* cited by examiner

COATING SYSTEM WITH AN ULTRASONIC HEAD

TECHNICAL FIELD OF THE INVENTION

This invention relates to a coating system for coating a workpiece with a liquid coating product.

BACKGROUND OF THE INVENTION

Ultrasonic liquid atomization has been used so far for spraying a liquid coating product onto a workpiece to be coated. In "Ultrasonic Liquid Atomization Theory and Application" (Partridge Hill Publishers—1998 and 2006) Harvey L. Berger considers the application of electrostatics to ultrasonic liquid atomization and explains that implementing electrostatics onto ultrasonic atomization would theoretically bring a very high efficiency to the control of the spray application, even with voltage much lower than those used in conventional electrostatic spraying.

Since then, some applications of ultrasonic atomization with electrostatics have been considered. For instance, in a paper "Deposition of $CuInS_2$ films by electrostatic field assisted ultrasonic spray pyrolysis" (Solar Energy Materials and Solar Cells 95 (2011) 245-249), Dong-Yeup Li and JunHo Kim discloses a case where a liquid to be sprayed is excited by an ultrasonic probe in order to be converted into an aerosol which is conveyed by a carrying gas towards an outlet of a tube, in order to be used for spray pyrolysis deposition. Such a system does not allow precisely controlling the flow rate nor the density of the aerosol and, in its path between the bath where it is formed and the outlet of the tube, the aerosol might agglomerate, so that the size of the droplets used for coating an object cannot be accurately controlled because of coalescence generally observed between droplets. The coating might be rough or non homogeneous and some defects may be generated on the coated surface.

In "Deposition of Ni-CGO composite anodes by electrostatic assisted ultrasonic spray pyrolysis method" (Materials Research Bulletin 42 (2007) 1674-1682), Jing-Chiang Chen et al. consider creating an aerosol and conveying it in a glass tube toward an nozzle facing a copper plate which supports a substrate to be coated. Here again, there is a risk of agglomeration of the droplets of the aerosol.

These academic works would not be easy to use in an industrial environment because the coating deposition is highly dependent on many factors, such as the geometry and length of a tube conveying an aerosol.

On the other hand, in a known system, the electrostatic field is generally created between an electrode and the object to be coated, this electrostatic field having a field line distribution which is not optimized for the workpiece to be coated. Under such circumstances, a substantial part of the atomized product might end up outside of the surface to be coated, which is detrimental in terms of pollution and from an economic stand point.

SUMMARY OF THE INVENTION

The invention aims at solving these problems with a new coating system which makes use of the versatility of an ultrasonic head and which allows optimizing the distribution of electrostatic field lines, thus optimizing the coating efficiency.

To this end, the invention concerns a coating system for coating a workpiece with a liquid coating product, this coating system including:

- an ultrasonic spray head for generating droplets of coating product,
- an electrode for generating an electrostatic field between the electrode and the ultrasonic spray head and
- a high voltage generator connected to the electrode for supplying the electrode with high voltage.

Thanks to the invention, the electrode allows precisely controlling the electrostatic field line distribution towards the workpiece, thus the path of the coating product droplets towards the workpiece. More precisely, the electrode acts as a conformator for an electric field which guides the droplets towards the workpiece to be coated According to further aspects of the invention which are advantageous but not compulsory, the coating system might incorporate one or several of the following features, taken in any technically admissible combination:

- The shape of the electrode is configured on the basis of the geometry of the workpiece. Thanks to this aspect of the invention, the shape of the electrode can be customized according to the actual geometry of the workpiece to be coated, which allows building the electrostatic field lines closely around the workpiece, thus avoiding, or limiting to a great extent, an overspray phenomenon.
- An edge of the electrode is an image of the contour of the workpiece, as seen from the ultrasonic spray head, preferably an exact image of this contour.
- The coating system includes a metering device for feeding the ultrasonic head with liquid coating product in controlled amount, in particular in the form of a pump with a movable piston. Alternatively, other types of pumps can be used as metering devices.
- The electrode supports the workpiece and is in contact with the workpiece.
- The electrode is shaped according to the workpiece geometry and supported by a base part which includes the high-voltage generator.
- The base part insulates the workpiece from the ground potential, preventing any electrical leak from the electrode.
- The base part defines an area configured for accommodating electrodes of different shapes.
- An electrical contact member is located in the area for connecting the high voltage generator to an electrode accommodated in the area.
- The electrical contact member is movable along an axis non parallel to an electrode accommodated in the area and biased towards this electrode.
- The high voltage generator is integrated in a sub-module which includes also a discharge resistor and connection means, said sub-module defining two housings, where the high voltage generator and the discharge resistance are respectively received, and a connection housing, where a connector is received to connect the high voltage generator and the discharge resistor.
- The electrical contact is supported by, and electrically connected to, the connector received in the connection housing.
- The electrode is shaped to be at least partially surrounded by the workpiece.
- The electrode is rotatable around its longitudinal axis.
- The electrode is secured to the ultrasonic spray head and configured to charge the droplets by ionization.

The electrode is provided with spikes spread around a discharge nozzle of the ultrasonic spray head with a distribution based on the geometry of the workpiece.

An orientation angle of the spikes with respect to a central axis of the ultrasonic spray head is adjustable on the basis of the geometry of the workpiece and/or of a distance between the electrode and the workpiece.

The electrode is formed by the workpiece.

The ultrasonic head is provided with an air ejection unit configured to deliver a jet of shaping air around the droplets leaving the ultrasonic head.

BRIEF DESCRIPTION OF THE DRAWINGS

The invention will be better understood on the basis of the following description which is given in correspondence with the annexed figures and as an illustrative example, without restricting the object of the invention. In the annexed figure.

DETAILED DESCRIPTION OF SOME EMBODIMENTS

The coating system 2 represented in FIGS. 1 to 7 includes an enclosure 4 which defines an internal volume V4 closed by a door 6 provided with a transparent window 8 made of mineral or organic glass, which allows checking volume V4 through door 6.

Alternatively, door 6 is not transparent.

Enclosure 4 forms a cabin for a coating process to be implemented with coating system 2.

Coating system 2 also includes a control cabinet 10 which comprises, amongst others, a programmable logic controller or PLC 12. On FIG. 1, the front panel of control cabinet 10 has been removed in order to show PLC 12.

Coating system 2 includes an ultrasonic spray head 14 which is supported by a 3 axis Cartesian robot and which has its longitudinal axis X14 oriented vertically. Ultrasonic head is directed downwardly towards a workpiece W1 to be coated which lies underneath ultrasonic spray head 14.

In another embodiment, the spray head can be handled by a six axis robot allowing that axis X14 presents an angle with the vertical for an optimal position of the spray head in front of the workpiece surface to be coated, especially for volumic/3D workpieces.

The ultrasonic head frequency can be chosen in the whole ultrasonic frequency range from 20 kHz to 10 MHz, and for instance at the following frequencies: 25 kHz, 35 kHz, 48 kHz, 60 kHz, 120 kHz, 180 kHz, 250 kHz. The size of the droplets generated by ultrasonic spray heads, expressed in Number Median Diameter (NMD or DN0.5) are typically given as follows: 69 μm (25 khz), 50 μm (35 kHZ), 38 μm (48 kHZ), 32 μm (60 kHZ), 18 μm (120 kHZ), 12 μm (180 kHZ), 8 μm (250 kHZ).

Ultrasonic spray head 14 may be of any commercially available type.

A pipe 18 feeds ultrasonic spray head 14 with a liquid to be atomized and a non-represented vibrating member integrated within ultrasonic spray head 14 is actuated to atomize this coating product when workpiece W1 is actually located under ultrasonic spray head 14. On FIG. 2, arrows F2 represent the flow of droplets of atomized coating product coming out of ultrasonic spray head 14 and directed towards workpiece W1.

Figure 1:
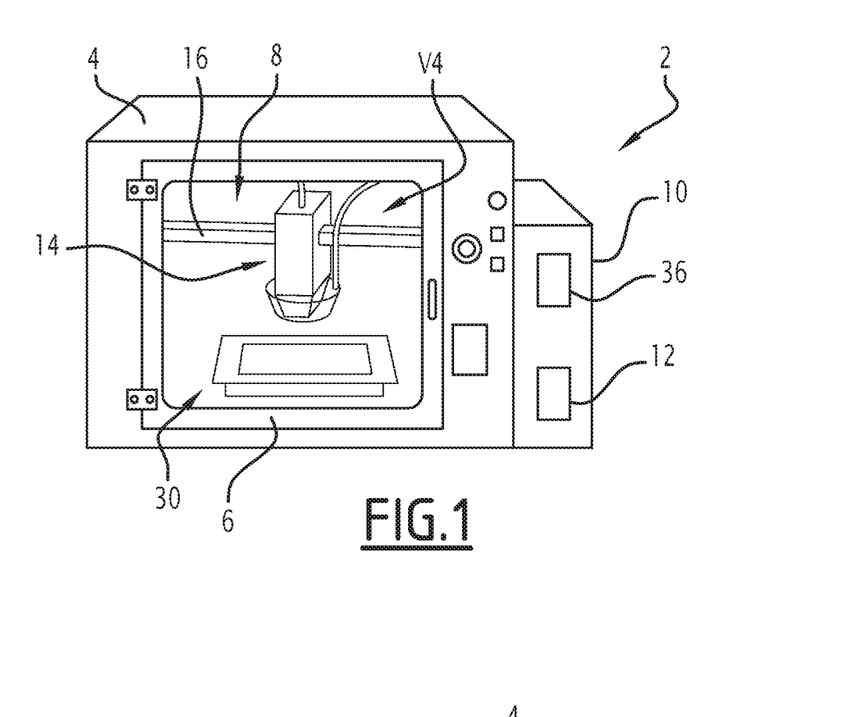
FIG. 1 is a perspective view of a coating system according to the invention.

Pipe 18 is fed with coating product from a metering pump 19 visible on FIG. 1 only and represented as a syringe. Preferably, metering pump 19 has a movable piston. Alternatively, other types of metering devices can be used to feed ultrasonic spray head 14 via pipe 18, such as a gear pump. Using a metering device to feed ultrasonic spray head 14 allows a precise control of the amount of coating product, thus a precise control of flow F2 of droplets.

In order to better control the shape of the spray of droplets exiting ultrasonic spray head 14, a shaping gas unit 20 is mounted around the lower extremity of ultrasonic spray head 14. This shaping gas unit 20 is fed with air via a pipe 22 and expels a flow of air, represented by arrows F4 on FIG. 2, around the flow of droplets F2. This avoids that this flow diverges radially with respect to axis X14. Alternatively, a gas different from air can be used in shaping gas unit 20.

Ultrasonic spray head 14 is movable in three directions of the space with a 3 axis Cartesian robot represented by a guide rail 16.

In order to enhance the effectiveness of the coating of workpiece W1, an electrostatic field E is generated between ultrasonic spray head 14 and an electrode.

To this end, an electrode module 30 is located within volume V4, together with ultrasonic spray head 14 and the 3 axis Cartesian robot. The electrode module 30 supports workpiece W1. In other words, workpiece W1 lies on electrode module 30. Workpiece W1 is electrostatically charged by contact with electrode 32A.

This electrode module 30 has a flat upper surface constituted by an electrode 32A made of a sheet of electrically conductive material, in particular a metal, such as a ferrous metal (steel, stainless steel . . . ) or a non-ferrous metal (aluminum, copper . . . ) and their alloys.

This electrode 32A lies on a base part 34 of electrode module 30, which is made of an electrically insulating material, such as a synthetic material, for instance polypropylene (PP), polyoxymethylene (POM), polytetrafluoroethylene (PTFE), polyvinylidene difluoride (PVDF), polyvinyl chloride (PVC). Base part 34 insulates workpiece W1 and electrode 32A from the ground potential, preventing any electrical leak from the electrode.

Figure 4:
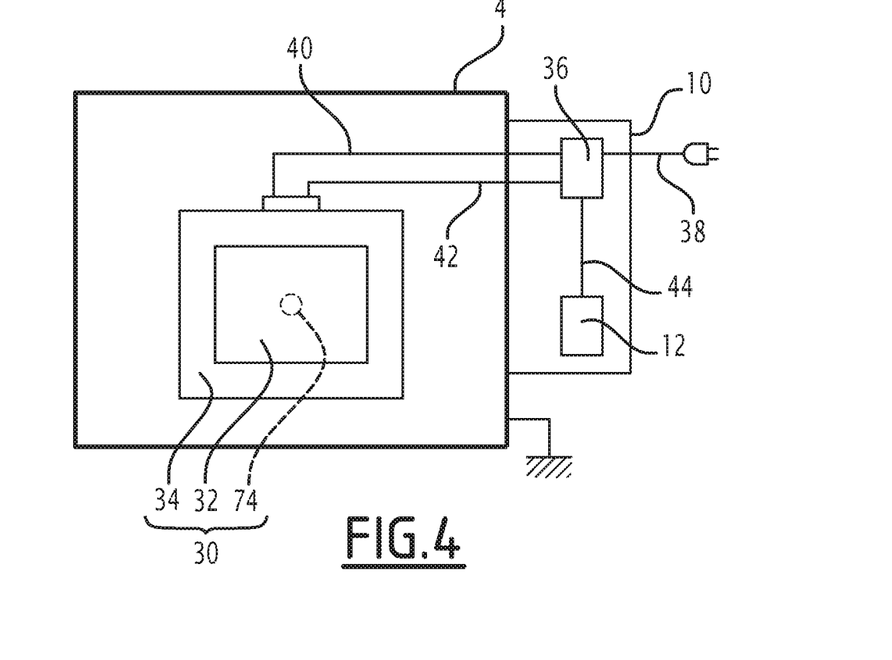
FIG. 4 is a schematic representation of the wiring used for controlling an electrode module of the system of FIGS. 1 to 3.
Figure 5:
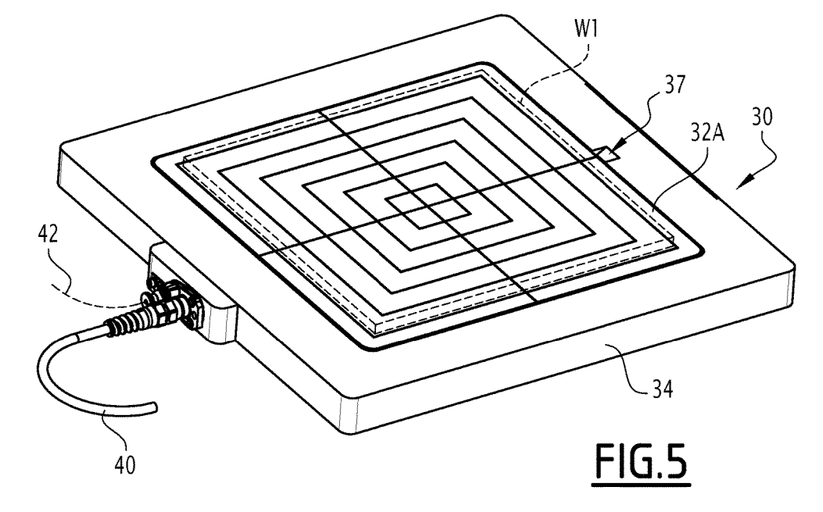
FIG. 5 is a perspective view of the electrode module in a first configuration of use corresponding to the configuration of the system on FIG. 2.
Figure 6:
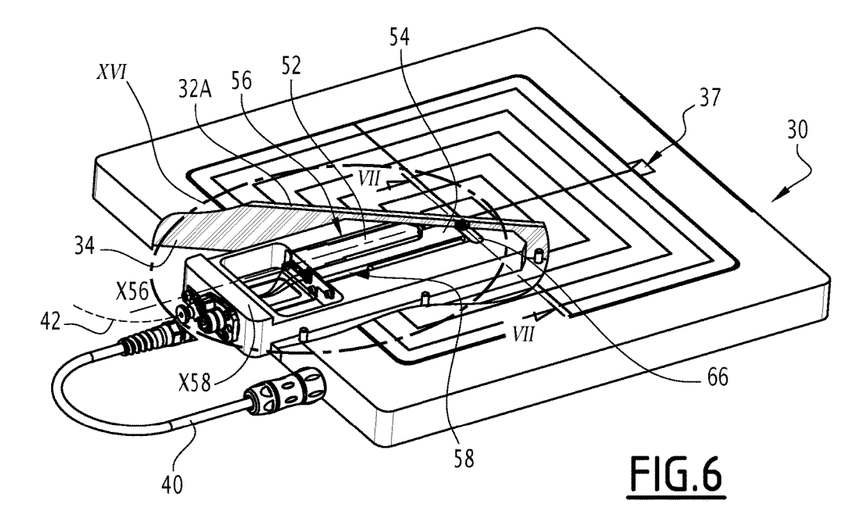
FIG. 6 is a cut-away view of the electrode module in the configuration of FIG. 5.
Figure 7:
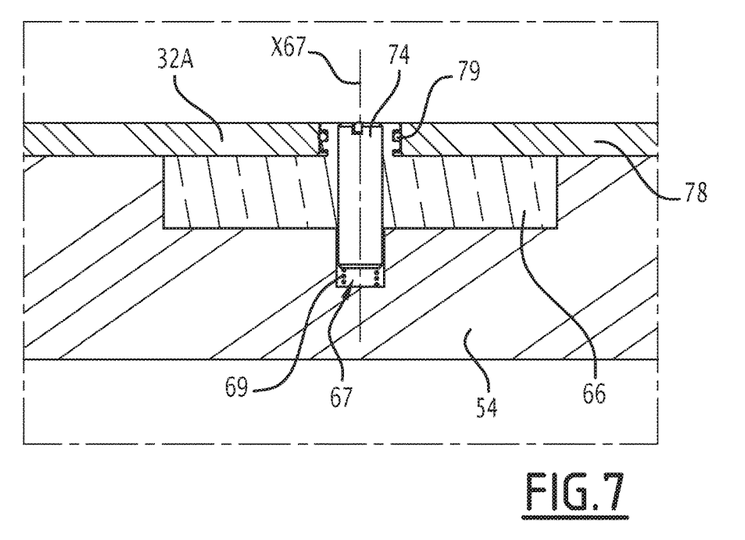
FIG. 7 is an enlarged partial cut view along line VII-VII on FIG. 6.
Figure 8:
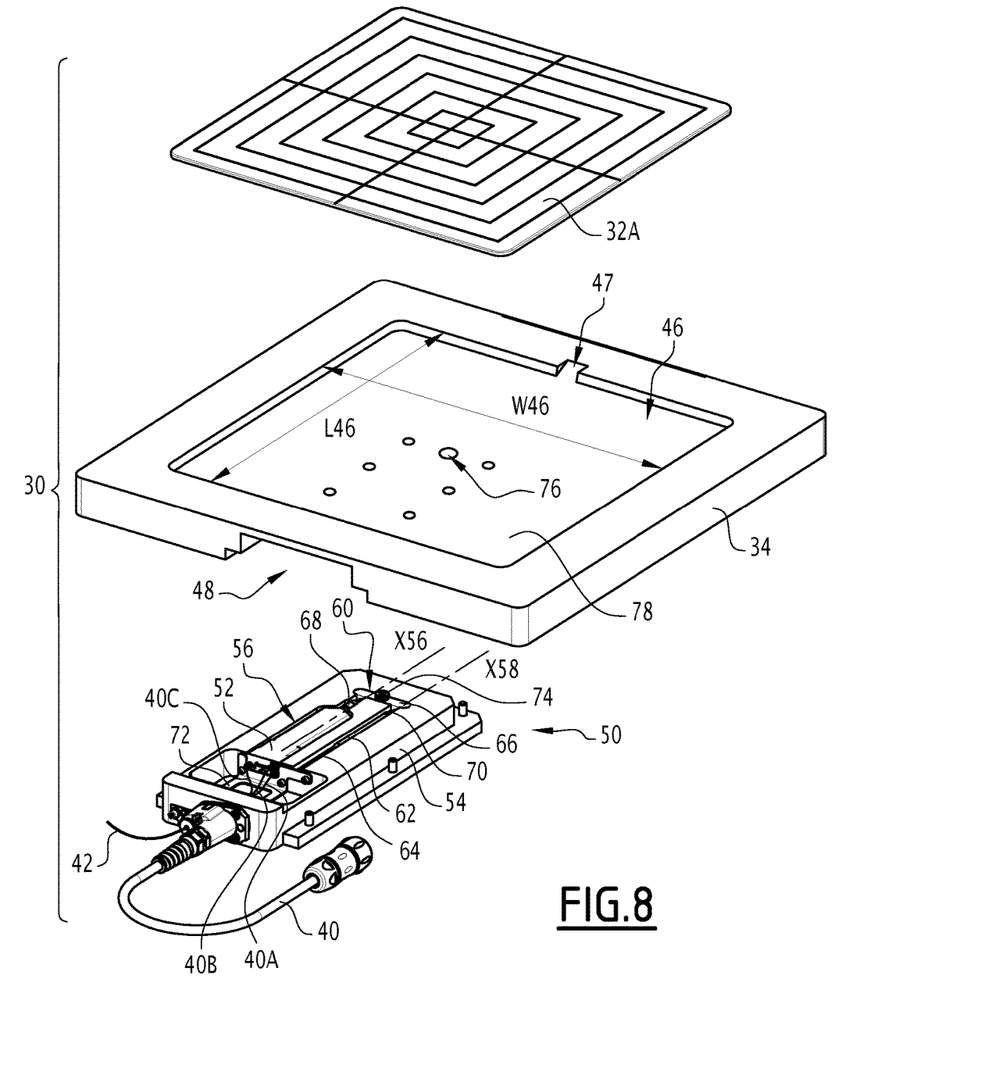
FIG. 8 is an exploded view of the electrode module.

As shown on FIG. 4, electrode module 30 is controlled by a high voltage controller 36 located in control cabinet 10. More precisely, high voltage controller 36 is connected to a power grid via a first cable 38 and to electrode module 30 via a second cable 40. A third ground cable 42 connects electrode module 32 to enclosure 4, which is grounded.

On the other hand, a control cable 44 allows PLC 12 to control high voltage controller 36 according to a pre-established control sequence and in a way consistent with applicable safety rules.

Ultrasonic spray head 14 is grounded via a non represented grounding cable and a non represented ultrasonic connector, which can be considered as "double grounding". Actually, this is important insofar as the vibrating member of ultrasonic spray head 14 is an electrical device whose operation could be disturbed if it were submitted to a high voltage. Thus, the general layout of coating system 2, where high voltage is applied at the level of electrode module 30, not at the level of ultrasonic spray head 14, is advantageous.

When electrode module 30 is supplied with an electrical current via second cable 40, electrostatic field E is generated between ultrasonic spray head 14 and electrode 32. Electrostatic field lines L extend between ultrasonic spray head 14, on the one hand, and electrode 32 and workpiece W1, on the other hand.

Electrode 32A is charged, with a high voltage in the range between 0.1 kV and 100 kV, and preferably between 5 kV and 30 kV. Assuming the high voltage is negative, the droplets of atomized coating product exiting ultrasonic spray head 14 are charged positively by influence, so that they follow the field lines L towards electrode 32, thus towards workpiece W1 which lies on top of electrode 32A.

In the example of FIG. 2, workpiece W1 is a flat piece, for instance a solar cell glass cover. On FIG. 5, workpiece W1 is represented in chain-dotted lines in order to fully show electrode 32A.

In such a case, the shape of electrode 32A is flat and rectangular, with an edge having substantially the same shape as the edge of workpiece W1, as shown on FIG. 5.

For instance, electrode 32A can be a rectangle with the same proportions as the rectangle defined by workpiece W1 and with a surface area S32 comprised between 80% and 5000%, preferably between 100% and 125%, of the surface area SW of the workpiece W1.

More precisely, surface area S32 can be smaller than or equal to surface area SW, with the ration S32/SW in the range between 0.8 and 1. Alternatively, surface areas S32 and SW can be equal or substantially equal, with ratio S32/SW in the range between 0.95 and 1.05. According to another approach, surface area S32 may be larger than or equal to surface area SW, with ratio S32/SW in the range between 1 and 50.

Under such circumstances, the portion of electrode 32A which is "visible" from ultrasonic spray head 14 around workpiece W1 can be reduced like in the configuration of FIG. 2, so that all the field lines L end up and close around workpiece W1. Thus, droplets coming out of ultrasonic spray head 14 are efficiently directed by electrostatic field E towards workpiece W1.

As can be derived from FIGS. 5 to 10, base part 34 defines a top cavity 46 which forms an area with a length L46 and a width W46 corresponding to the maximum dimensions of an electrode 32A and any other electrode to be used in electrode module 30.

In the configuration of FIGS. 2, 5 6 and 8, electrode 32A has the maximum possible dimensions, so that it fills cavity 46 up. A notch 37 allows accessing laterally cavity 46 to exert a lifting effort on electrode 32A when it must be separated from base part 34, e.g. with a tool such as the tip of a screwdriver or even the finger tip.

Base part 34 also defines a recess 48 which accommodates a sub-module 50 adapted to convert the current received from high voltage controller 36 via second cable 40 into a high voltage to be applied to electrode 32.

Sub-module 50 includes a high voltage generator 52 made by a cascade of diodes, according to a known technique in the field of electrostatic spraying, in particular in hand guns. Sub-module 50 includes an insulative body 54 which defines a first elongated housing 56 extending along a first axis X56. Body 54 also defines a second elongated housing 58 which extends along a second axis X58 parallel to axis X56. Actually, axes X56 and X58 can be non-parallel with any orientation. In a preferred configuration, axes X56 and X58 are substantially parallel, that is converge or diverge with an angle between them of less than 30°, so that they open out on the same side of body 54. This configuration makes a very neat connection since the second supply cable 40 may bring together the high voltage power and the grounded reference. A connection housing 60 connects housings 56 and 58 perpendicularly to axes X56 and X58. Thus, housings 56, 58 and 60 together define a U shaped volume for accommodating the high voltage supply means of sub-module 50.

A discharge resistor 62 is located within housing 58, together with a connecting rod 64. On the other hand, a connector 66 is accommodated within housing 60.

A spring 68 is interposed between high voltage generator 52 and connector 66. Another spring 70 is interposed between connector 66 and resistor 62. Thus, connector 66 connects high voltage generator 52 and discharge resistor 62 with the help of springs 68 and 70.

A ground plate 72 is located at one end of body 54 where housings 56 and 58 open out, opposite from housing 60. This allows connecting high voltage generator 52 and connecting rod 64 to the ground via third ground cable 42, whereas high voltage generator 52 is also connected to second cable 40 via individual conductors 40A, 40B and 40C. For the sake of clarity, connectors 40A, 40B and 40C are represented only on FIG. 8.

Connector 66 bears a contact member 74 which goes through an opening 76 of a wall 78 of base part 34 separating cavity 46 from recess 48. Thus, when sub-module 50 is mounted within recess 48, contact member 74 is flush with wall 78 or protrudes into cavity or area 46, so that it can apply to any electrode installed within cavity or area 46 a high voltage originating from high voltage generator 52.

As shown on FIG. 7, contact member 74 is formed by an electrically conductive stud housed in a vertical bore 67 of connector 66. Connector 66 is immobilized within wall 78 by an O-ring 79. The vertical position of contact member 74 within bore 67 can be adjusted along the central axis X67 of bore 67. A spring 69 is advantageously provided at the closed end of bore 67, which biases stud against electrode 32A.

As can be derived from FIGS. 5, 6, 9 and 10, electrodes with different geometries can be used with base part 34 and sub-module 50.

Figure 2:
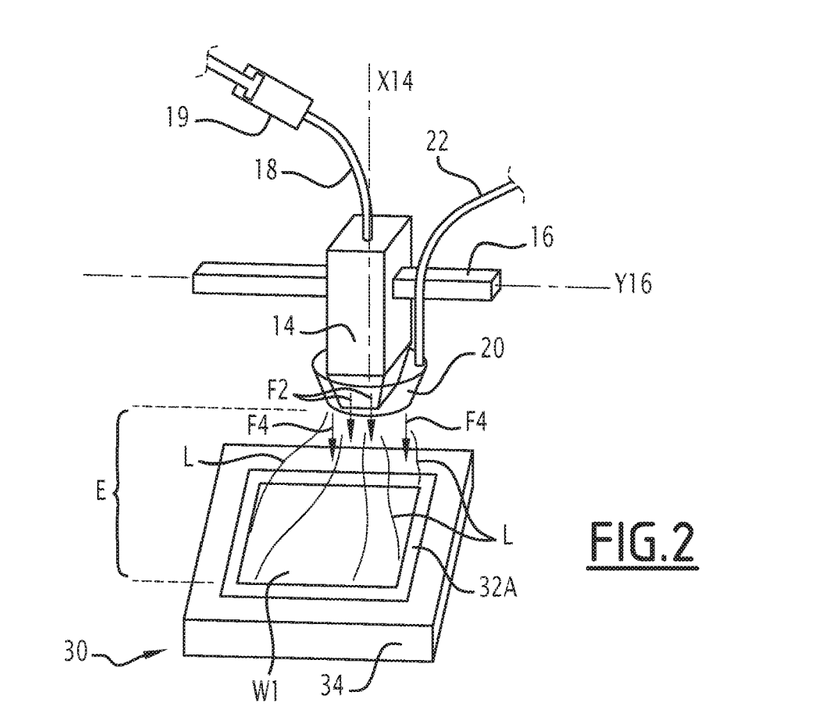
FIG. 2 is a perspective view, on a larger scale, of some components of the system of FIG. 1, in a first configuration of use.
Figure 9:
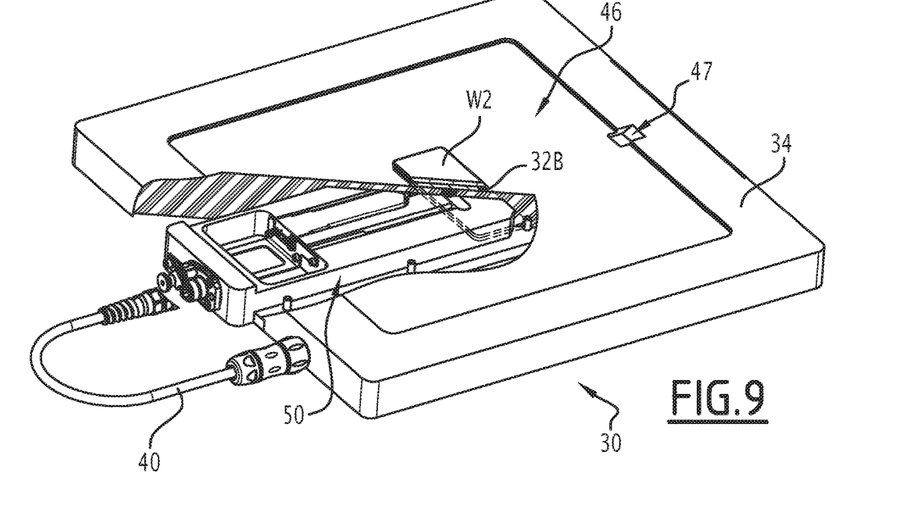
FIG. 9 is a cut-away view similar to FIG. 6 when the electrode module is in a second configuration of use.

For example, the rectangular electrode 32A used in the configuration of FIG. 2 for a large workpiece W1 of a rectangular shape can be replaced with an electrode 32B having a flat and rectangular shape adapted to a workpiece W2 with smaller dimensions, such as a screen of a cellphone, as shown on FIG. 9. Provided that electrode 32B is positioned in the center part of cavity 46, so that it contacts contact member 74, this electrode is also suitable for creating an electrostatic field with ultrasonic spray head 14, so that the operation described with respect to FIG. 2 can be obtained an electrostatic field lines close on electrode 32B around workpiece W2.

Figure 3:
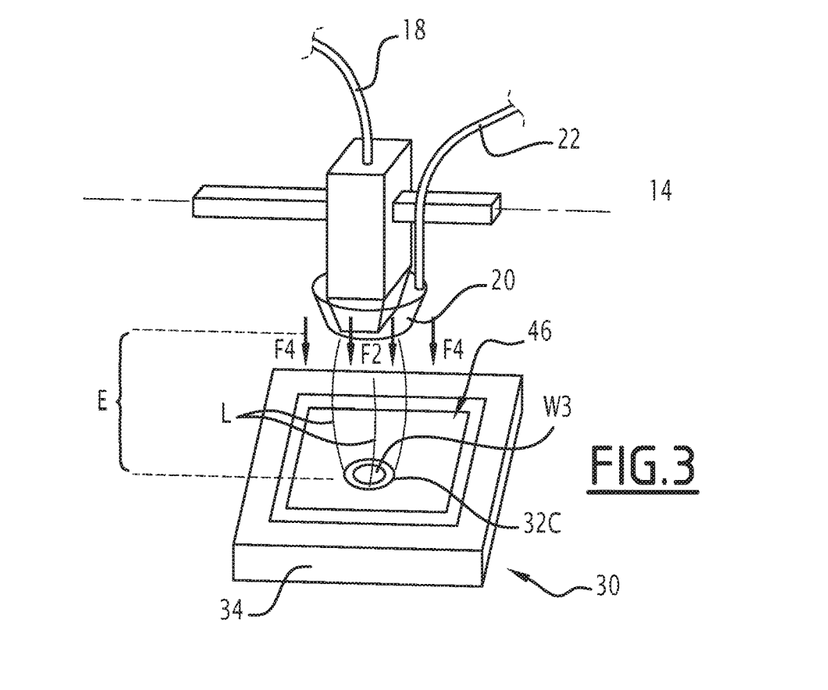
FIG. 3 is a perspective view similar to FIG. 2 when the system is in a second configuration of use.
Figure 10:
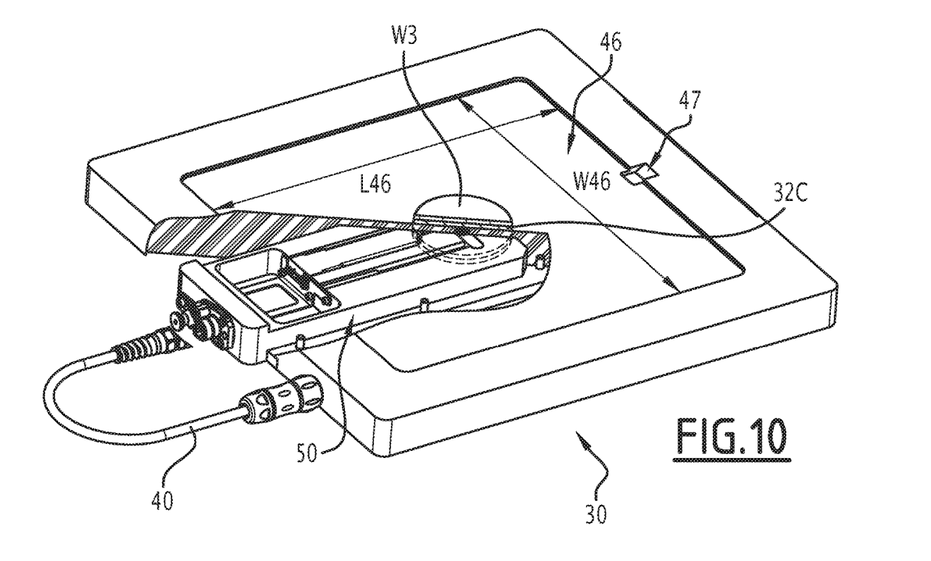
FIG. 10 is a cut away view similar to FIG. 6 when the electrode module is in a third configuration of use corresponding to the configuration of the system on FIG. 3.

An electrode 32C can also be used in case a workpiece W3, in the form of a disc or a portion of a sphere, is used, as shown on FIGS. 3 and 10. For example, the workpiece W3 can be an optical lens to be coated with different coating layers such as a hydrophobic layer, a top coat protective layer, a hard coating or even anti-reflective coating layers. If workpiece W3 is a disc, electrode 32C is flat. If workpiece W3 is in the form of a portion of a sphere, electrode 32C is preferably curved or warped to conform to the shape of workpiece W3. In this second case, electrode 32C may protrude upwardly with respect to cavity 46, which still forms an area for accommodating electrode 32C.

On FIGS. 9 and 10, for easier understanding, the global shape of workpieces W2 and W3 and the global shape of electrodes 32B and 32C are shown partly in dotted lines.

As shown on FIG. 3, the electrostatic field E established between electrode 32C and ultrasonic spray head 14, which is grounded, gives rise to field lines L which extend between items 14 and 32C, so that the droplets leaving ultrasonic spray head 14 in the form of flow F2 are guided by these field lines towards workpiece W3.

In this example, the ratio of the respective diameters of workpiece W3 and electrode 32C can be chosen between 0.8 and 2.

Other shapes can be selected for the electrode placed on area 46, depending on the actual geometry of the workpiece to be treated. For instance, a triangular electrode or a polygonal electrode, with more than four sides, can be manufactured in order to follow the contour of the workpiece to be treated which can be polygonal or rounded, in particular with an oval shape. Also, a tridimensional or curved shape design of the electrode can be chosen. For instance, a hemispherical or paraboloid electrode can be designed in order to support a hemispherical or paraboloid optical lens. By extension, any volumic regular or irregular shape electrode can be chosen depending on the geometry of the workpiece to be treated.

Actually, the edge of the electrode 32A, 32B, 32C or equivalent is advantageously an image of the contour of the workpiece, as seen from ultrasonic spray head 14. In other words, the edge of the electrode can be defined so as to evenly distribute the droplets around the contour of the workpiece, and increase the transfer efficiency of the product to the workpiece.

Advantageously, the edge of the electrode 32A, 32B or 32C is an exact image of the contour of the workpiece, where "exact image" means that the difference between an area of a surface bordered by the edge of the electrode and an area bordered by the contour of the workpiece is less than 10% of the area bordered by the contour.

On the other hand, the geometry of the electrode 32A, 32B or 32C can be adapted by increasing the exposed surface of the electrode in this region, the exposed surface of the electrode being the surface which is visible around the workpiece from ultrasonic spray head 14, so as to precisely control the coating profile on the edge of the workpiece.

In the second, third and fourth embodiments of the invention represented on FIGS. 11 to 15, the parts similar to the ones of the first embodiment bears the same reference and are not explained in detail. Hereafter, mainly the differences with the first embodiment are explained.

Figure 11:
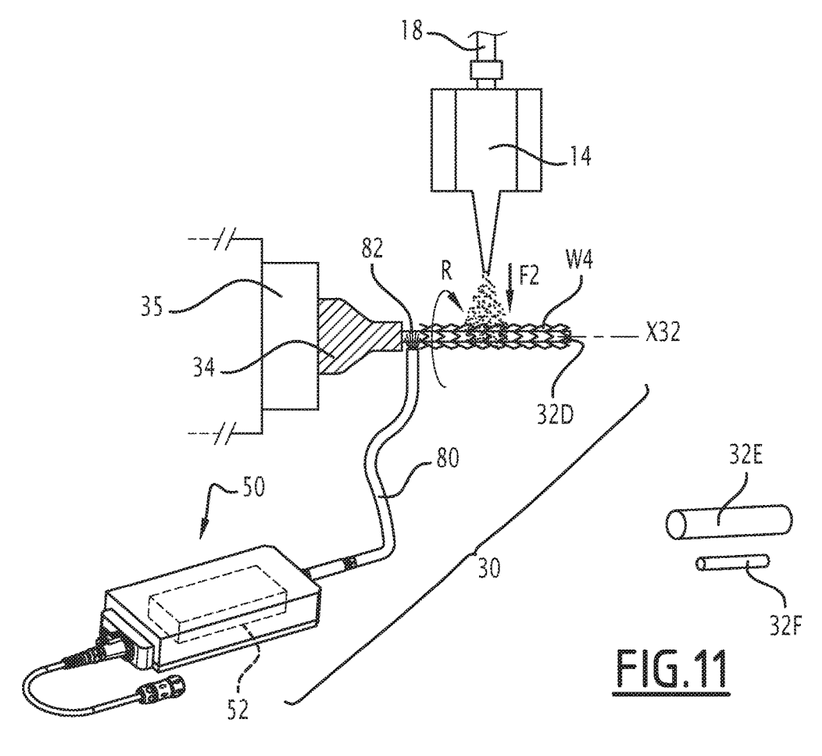
FIG. 11 is a schematic representation of a coating system according to a second embodiment of the invention.

In the second embodiment of FIG. 11, the workpiece W4 to be coated is a vascular stent. In such a case, the electrode 32D is shaped as a mandrel which extends along a longitudinal axis X32 and which is held by an insulating base part 34, and driven in rotation around this axis by a mechanism included in a support part 35. Electrode 32D is cylindrical and shaped to be totally or partially surrounded by stent W4.

The sub-module 50 which includes the high voltage generator 52 is located outside the base part 34 and connected to the electrode 32D by a cable 80 ending with a conductive brush 82 in sliding contact with the outer peripheral surface of electrode 32D.

As can be seen on the right of FIG. 11, some other mandrels 32E, 32F can be used with parts 34, 35 and sub-module 50 of electrode module 30, depending on the geometry of the stents W4 to be coated.

Alternatively, electrodes 32D to 32E can be non cylindrical, depending on the shape of the workpieces W4 to be coated.

Figure 12:
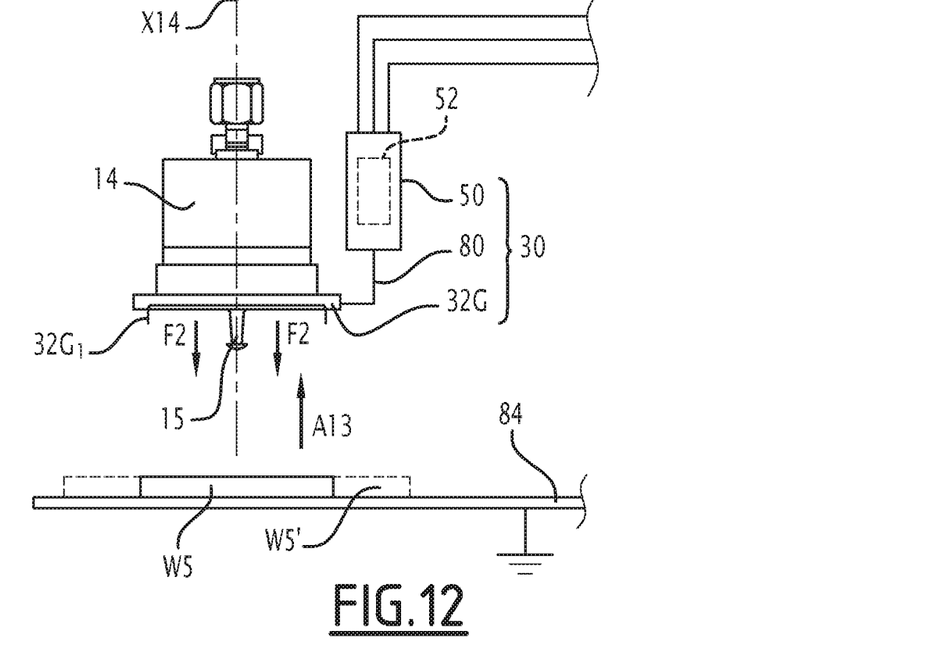
FIG. 12 is a front view of a coating system according to a third embodiment of the invention.
Figure 13:
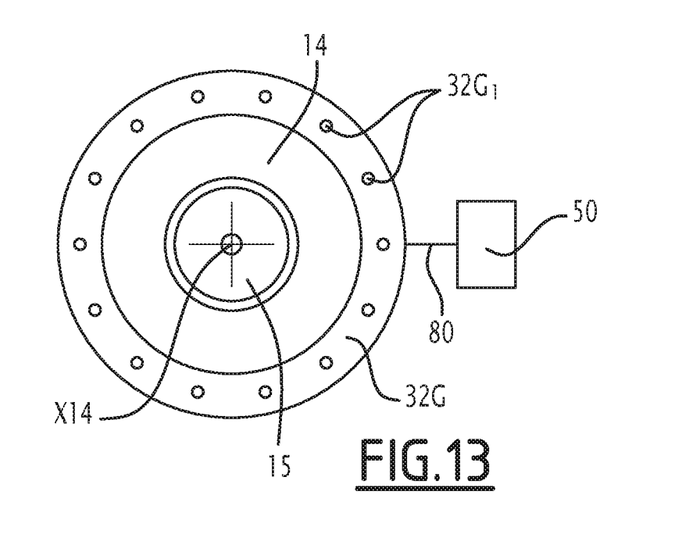
FIG. 13 is a view in the direction of arrow A13 on FIG. 12.
Figure 14:
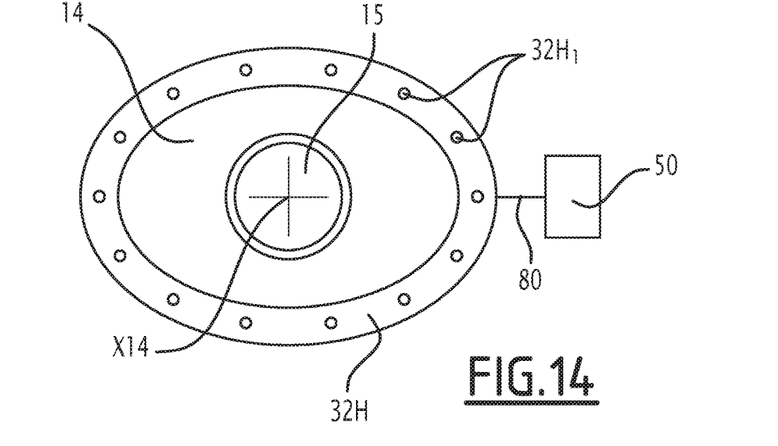
FIG. 14 is a view similar to FIG. 13 when the coating system of this third embodiment is in another working configuration.

In the third embodiment of the invention represented on FIGS. 12 to 14, electrode 32G is mounted around ultrasonic spray head 14 and supplied with high voltage via a sub-module 50 of electrode module 30 which includes a high-voltage generator 52. In such a case, the flow F2 of droplets coming out of a discharge nozzle 15 of ultrasonic spray head 14 is electrostatically loaded by Corona effect, that is by ionization of air around nozzle 15, thanks to spikes 32$G_1$ of electrode 32 which extends towards a workpiece W5 to be coated which lies on a grounded plate 84.

When workpiece W5 is circular as shown in solid line on FIG. 12, electrode 32G is also circular and its spikes 32$G_1$ are regularly distributed around the longitudinal axis X14 of ultrasonic spray head 14, as shown on FIG. 13.

When workpiece W5 has an oval shape as shown with reference W5' on FIG. 12, then the electrode can be also shaped as an oval, as shown on FIG. 14 with electrode 32H. Its spikes 32H1 can be regularly or non-regularly distributed around discharge nozzle 15 and central axis X14 of ultrasonic head 14 in order to evenly or unevenly distribute the droplets on the surface of workpiece W5' to be coated.

Figure 15:
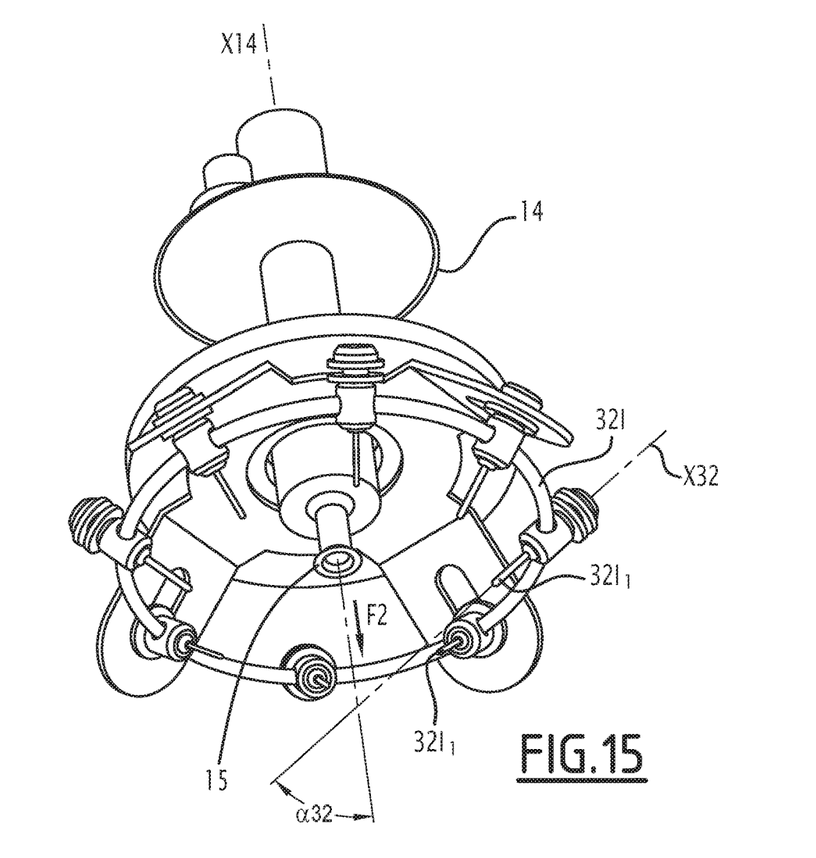
FIG. 15 is a partial perspective view of a coating system according to a fourth embodiment of the invention.
Figure 16:
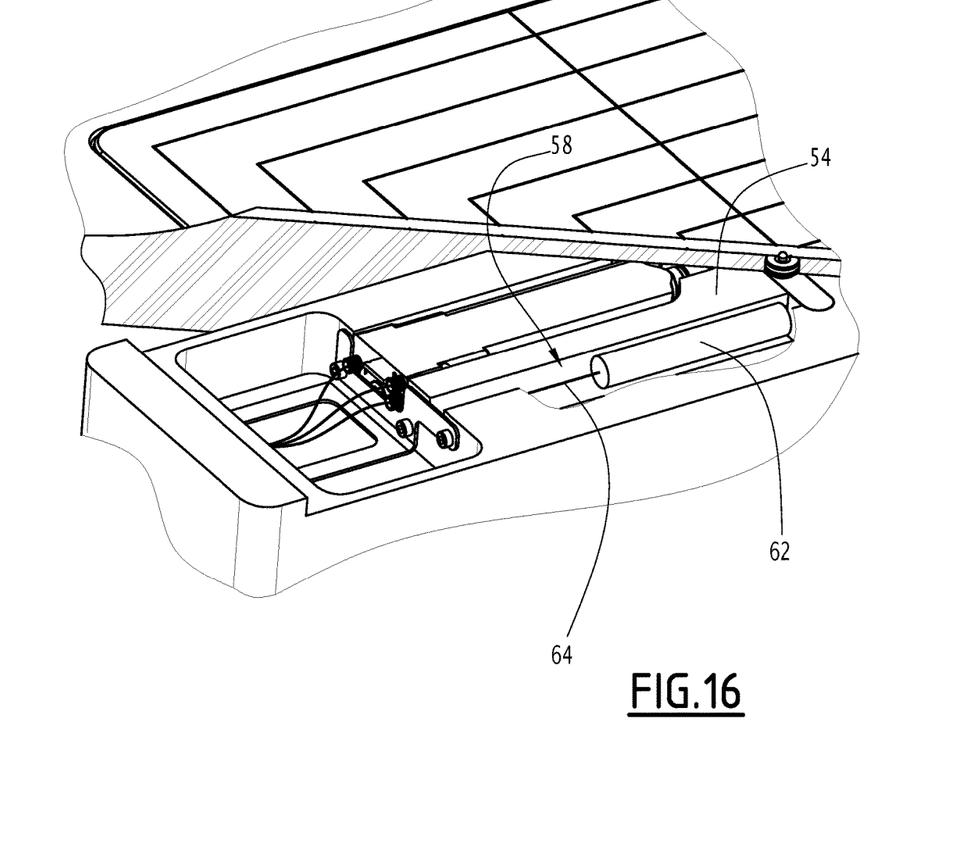
FIG. 16 is a detailed cut-away view of the electrode module of FIG. 6.

As shown on FIG. 15, the spikes 32$I_1$ of an electrode 32I may converge towards the central axis X14 and the nozzle 15 of the ultrasonic spray head 14 in the direction of the flow F2 of droplets.

$\alpha$32 denotes an angle between the central axis X14 of ultrasonic spray head 14 and a longitudinal axis X32 of a spike 32*h*. This angle is adjustable depending on the geometry of the workpiece to be coated and/or on a distance, measured along axis X14, between electrode 32I and the workpiece. Angle $\alpha$32 is an orientation axis of a spike 32$I_1$ with respect to axis X14.

According to a non represented alternative embodiment, the electrode may be formed by the workpiece itself. For instance, in the first and second embodiments, workpiece W1 to W4 may be in direct electrical contact with contact member 74 or with brush 82.

The features of the embodiments and variants considered here-above can be combined in order to generate new embodiments of the invention.

In particular, an air ejection unit similar to shaping gas unit 20 can be used in the second to fourth embodiments.

The invention claimed is:

1. A coating system for coating a workpiece with a liquid coating product, the coating system including an ultrasonic spray head for generating droplets of coating product, wherein the coating system further includes:
   an electrode for generating an electrostatic field between the electrode and the ultrasonic spray head, and
   a high-voltage generator connected to the electrode for supplying the electrode with high voltage, wherein the high-voltage generator is integrated in a sub-module which also includes a discharge resistor and a connector, said sub-module defining two housings, where the high-voltage generator and the discharge resistor are respectively received, and a connection housing where the connector is received to connect the high-voltage generator and the discharge resistor,
   and wherein the electrode is shaped according to a geometry of the workpiece and supported by a base part which includes the high-voltage generator.

2. The coating system according to claim 1, wherein a shape of the electrode is configurable on the basis of a geometry of the workpiece.

3. The coating system according to claim 1, wherein an edge of the electrode is an image of a contour of the workpiece as seen from the ultrasonic spray head.

4. The coating system according to claim 1, wherein the electrode supports the workpiece and is in contact with the workpiece.

5. The coating system of claim 1, wherein the base part insulates the workpiece from ground potential, preventing any electrical leak from the electrode.

6. The coating system of claim 1, wherein the base part defines an area configured for accommodating electrodes of different shapes.

7. The coating system of claim 6, wherein an electrical contact member is located in an area for connecting the high voltage generator to the electrode accommodated in the area.

8. The coating system according to claim 7, wherein the electrical contact member is movable along an axis non parallel to the electrode accommodated in the area and biased towards the electrode.

9. The coating system according to claim 1, wherein the electrode is shaped to be at least partially surrounded by the workpiece.

10. The coating system according to claim 9, wherein the electrode is rotatable around its longitudinal axis.

11. The coating system according to claim 1, wherein the electrode is secured to the ultrasonic head and configured to charge the droplets by ionization.

12. The coating system according to claim 11, wherein the electrode is provided with spikes spread around a discharge nozzle of the ultrasonic spray head with a distribution based on a geometry of the workpiece.

13. The coating system according to claim 12, wherein an orientation angle of the spikes with respect to a central axis of the ultrasonic spray head is adjustable on the basis of a geometry of the workpiece or on the basis of a distance between the electrode and the workpiece or on the basis of the geometry of the workpiece and the distance between the electrode and the workpiece.

14. The coating system according to claim 1, wherein the electrode is the workpiece.

15. The coating system according to claim 1, wherein the ultrasonic head is provided with an air ejection unit configured to deliver a jet of shaping air around the droplets leaving the ultrasonic head.

16. The coating system of claim 3, wherein the edge of the electrode is an exact image of the contour of the workpiece as seen from the ultrasonic spray head.

17. The coating system according to claim 1, wherein the coating system includes a metering device for feeding the ultrasonic head with liquid product in controlled amount.

18. The coating system of claim 1, wherein an electrical contact member is located in an area for connecting the high-voltage generator to the electrode accommodated in the area, and wherein the electrical contact member is supported by, and electrically connected to, the connector received in the connection housing.

19. The coating system of claim 18, wherein the electrical contact member is formed by an electrically conductive stud housed in a vertical bore of the connector.

20. The coating systems of claim 19, wherein an electrical contact member is located in an area for connecting the high-voltage generator to the electrode accommodated in the area, wherein the electrical contact member is movable along an axis non parallel to the electrode accommodated in the area and biased towards the electrode and wherein a spring is provided at a closed end of the bore and biases the stud against the electrode.

21. The coating system of claim 17, wherein the metering device is in the form of a pump with a movable piston.

* * * * *